US 8,140,481 B2

(12) United States Patent
Sato et al.

(10) Patent No.: US 8,140,481 B2
(45) Date of Patent: Mar. 20, 2012

(54) MEDICAL IMAGE FILING SYSTEM AND MEDICAL IMAGE FILING METHOD

(75) Inventors: Atsushi Sato, Tochigi-Ken (JP); Takashi Masuzawa, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 660 days.

(21) Appl. No.: 11/410,157

(22) Filed: Apr. 25, 2006

(65) Prior Publication Data
US 2006/0241979 A1    Oct. 26, 2006

(30) Foreign Application Priority Data
Apr. 26, 2005  (JP) .................................. 2005-127461

(51) Int. Cl.
*G06F 7/00* (2006.01)
(52) U.S. Cl. ........................ 707/653; 707/661; 382/131
(58) Field of Classification Search .................. 707/204, 707/661, 662, 665, 667, 653; 382/173, 131
See application file for complete search history.

(56) References Cited

U.S. PATENT DOCUMENTS

| | | | |
|---|---|---|---|
| 7,203,266 B2 * | 4/2007 | Fukuzawa .......................... | 378/4 |
| 2002/0019832 A1 * | 2/2002 | Tanaka et al. .................. | 707/500 |
| 2003/0095697 A1 * | 5/2003 | Wood et al. .................... | 382/131 |
| 2004/0087850 A1 * | 5/2004 | Okerlund et al. ............. | 600/407 |
| 2005/0036679 A1 * | 2/2005 | Wiemker et al. .............. | 382/173 |
| 2005/0110748 A1 * | 5/2005 | Boeing et al. .................. | 345/156 |
| 2005/0240445 A1 * | 10/2005 | Sutherland et al. ............... | 705/3 |
| 2006/0062485 A1 * | 3/2006 | Li et al. .......................... | 382/260 |
| 2006/0140334 A1 * | 6/2006 | Imaizumi et al. .................. | 378/4 |
| 2006/0173303 A1 * | 8/2006 | Yu et al. ......................... | 600/437 |

* cited by examiner

*Primary Examiner* — Amy Ng
(74) *Attorney, Agent, or Firm* — Oblon, Spivak, McClelland, Maier & Neustadt, L.L.P.

(57) ABSTRACT

A medical image filing system comprises a primary storage device and a secondary storage device. In addition, the medical image filing system comprising: an image secondary storage condition setting unit for presetting a secondary storage condition to secondarily store a medical image data to the secondary storage device; an image secondary storage determining unit for determining whether or not the medical image data recorded to the primary storage device satisfies the secondary storage condition set by the image secondary storage condition setting unit; and an image recording unit for recording the medical image data of the secondary storage object to the secondary storage device. Therefore, only medical image data of the secondary storage object is stored in the secondary storage device.

17 Claims, 8 Drawing Sheets

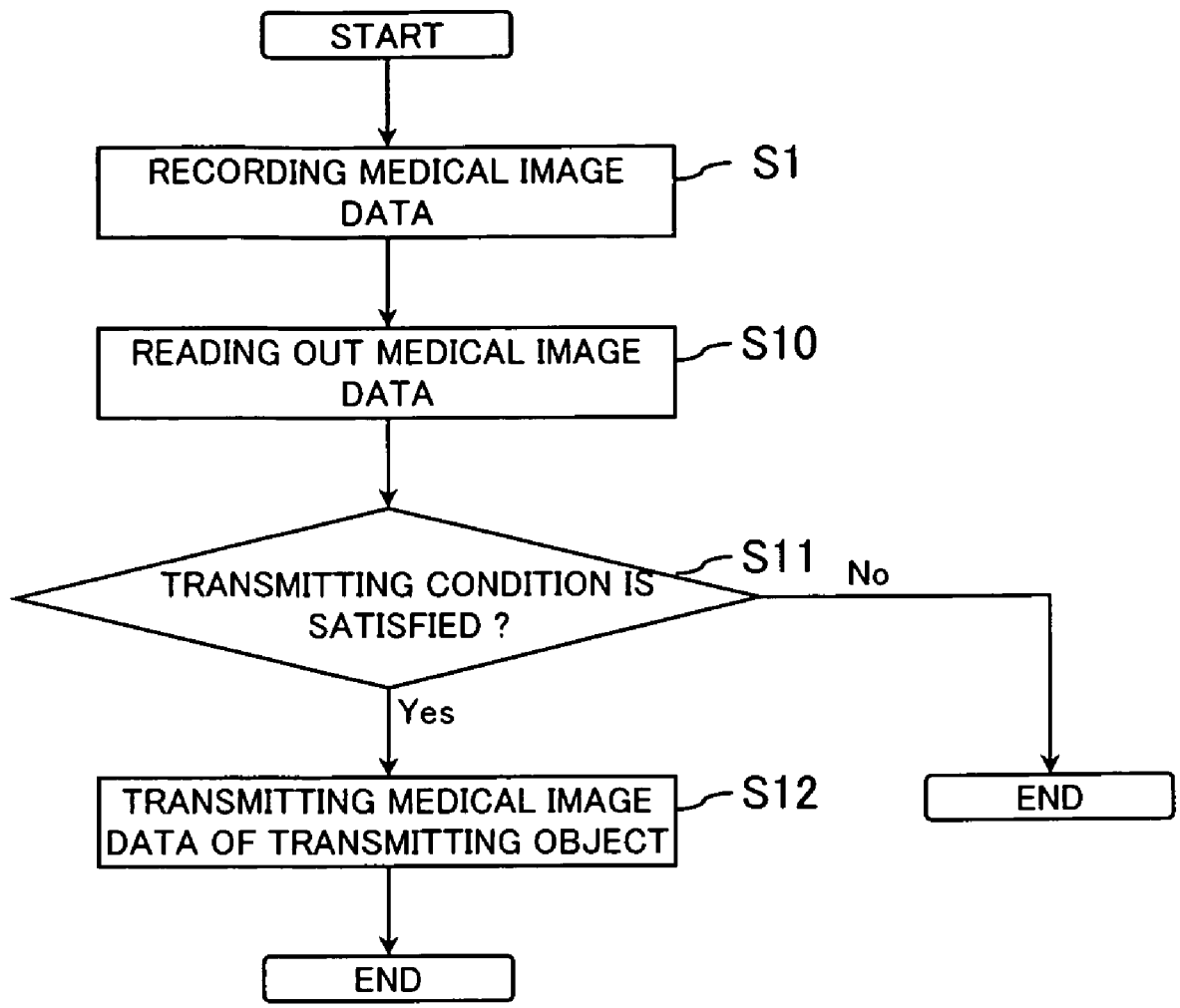
F I G. 5

| UID | PATIENT'S ID | MODALITY | ... | SLICE THICKNESS | ... | SECONDARY STORAGE OBJECT | DISPLAY OBJECT OF PROCESSED-IMAGE | CREATING OBJECT OF REFERENCE-IMAGE | DELETING OBJECT |
|---|---|---|---|---|---|---|---|---|---|
| 1.2.8329.1 | 1234 | CT | ... | 5 | ... | TRUE | FALSE | TRUE | FALSE |
| 1.2.8329.2 | 1234 | CT | ... | 1 | ... | TRUE | FALSE | FALSE | TRUE |
| 1.2.8329.3 | 1234 | CT | ... | 2 | ... | TRUE | TRUE | TRUE | FALSE |
| 1.2.8329.4 | 1133 | CT | ... | 1 | ... | TRUE | FALSE | FALSE | FALSE |

FIG. 7

MEDICAL IMAGE FILING SYSTEM AND MEDICAL IMAGE FILING METHOD

BACKGROUND OF THE INVENTION

1. Field of the Invention

The present invention relates to a medical image filing system and a medical image filing method that is incorporated in a PACS and stores (saves), transfers (distributes) and displays a medical image data. In particular, the present invention relates to a medical image filing system and a medical image filing method that preferably stores, transfers, and displays a large number of images collected with a modality (medical image tomography apparatus) of a multi-slice X-ray computerized tomography (CT).

2. Description of the Related Art

In general, a digital medical image data collected by a medical image tomography apparatus, such as an X-ray CT apparatus, are transferred to a PACS via a network. The PACS comprises a medical image filing system, and the transferred medical image data is received by the medical image filing system.

FIG. 8 is a block diagram showing the entire structure of a PACS using a conventional medical image filing system.

Referring to FIG. 8, a medical image filing system 101 comprises: a primary storage device 102; a reference-image storage device 103; a secondary storage device 104; and a server 105. The server 105 manages the output and input operation of a medical image data to/from the primary storage device 102, the reference-image storage device 103, and the secondary storage device 104. Therefore, specifically, the medical image data transferred from the medical image tomography apparatus 100 is processed by the server 105 as follows.

- Store the medical image data in the primary storage device 102 (a fast drive, such as an hard disc drive (HDD)) (function which primarily stores image)
- Store the medical image data stored in the primary storage device 102 to the secondary storage device 104 (media, such as a tape) (function which secondarily stores image)
- Transfer the medical image data stored in the primary storage device 102 to a medical image display device 107 or an image-processing device (not shown) via the network (function which transmits image)
- Display the medical image data stored in the primary storage device 102 on a first remote-terminal 106 (display a specific image with a Web technology: function which displays image).
- Convert the medical image data stored in the primary storage device 102 into image data in a general image format and store the converted medical image data to the reference-image storage device 103 (function which stores reference-image)
- Display the converted medical image data stored in the reference-image storage device 103 on a second remote-terminal 108 (display a simple image with the Web technology or refer to an in-hospital image: function which displays the reference-image)

However, with the above-mentioned conventional medical image filing system, all pieces of the medical image data created in the medical image tomography apparatus are primarily stored, are secondarily stored, and are transferred and are displayed. Therefore, the following inconveniences are serious.

That is, with the appearance of the multi-slice X-ray CT apparatus, a large number of images with an excessively thinner-slice-thickness can be captured for a short time, as compared with the conventional X-ray CT apparatus. Thus, with the same tomography range as the conventional tomography range, a larger number of slice images are created.

Further, with the same slice thickness as the conventional slice thickness, one-time tomography operation ends for a shorter time, as compared with the conventional tomography operation, and the number of tomography times increases. As a consequence thereof, the number of slice images created per unit time sharply increases and, in proportional to the increase, the amount of created medical image data sharply increases. In future, the increase in speed of the multi-slice X-ray CT apparatus and the reduction in slice thickness will advance and it is predicted that the amount of medical image data will sharply and continuously increase.

The above-mentioned sharp increase in amount of medical image data causes the following obvious problems of the medical image filing system.

- Shortage of capacity of the primary storage device (reduce a storing period on the on-line)
- Increase costs due to the increase in media, serving as the secondary storage devices.
- Delay the reference of image due to the extension of image transfer processing time and distributing processing time (display a specific image on the Web and display the image on the image display device)
- Reduce a network throughput due to in-hospital distribution of a large number of images
- Refer to unnecessary images on the reference of the simple image in the in-hospital distribution Usually, an examination image captured with the multi-slice X-ray CT includes a thick-slice image and a thin-slice image with the same tomography method or within the same tomography range (portion). The thick-slice image is referred to as a slice image, and the thin-slice image is used to obtain an image that can be easily interpreted in image processing including 3D processing and MPR processing. The image processing is performed immediately after the tomography operation (on the tomography day or in a few days after the tomography operation) and the image is additionally stored, as a processed image, in many cases. Rarely, the image that was captured is processed again. Further, upon referring to the simple image from sections in a hospital, the thin-slice image is not necessary.

SUMMARY OF THE INVENTION

The present invention has taken into consideration the above-described problems, and it is an object of the present invention to provide a medical image filing system and a medical image filing method such that a medical image data collected by a medical image tomography apparatus of a multi-slice X-ray CT apparatus makes it to filed efficiently. Accordingly, the medical image filing system and the medical image filing method avoid a problem like Shortage of capacity of the storage device, increase costs, delay the reference of image, reduce a network throughput, and refer to unnecessary images.

To solve the above-described problems, the present invention provides the medical image filing system, comprising: a primary storage device for primarily storing a medical image data; a secondary storage device for secondarily storing the medical image data; and a control unit for controlling a matter that the medical image data is stored in the secondary storage device on the basis of a property of the medical image data recorded to the primary storage device, or of the medical image data read out from the primary storage device.

To solve the above-described problems, the present invention provides the medical image filing system, comprising: a storage device for storing a medical image data; a control unit for controlling a matter that the medical image data is transmitted to an outside device on the basis of a property of the medical image data; and a transmitting unit for transmitting the medical image data that it is determined to be a transmitting object by the control unit.

To solve the above-described problems, the present invention provides the medical image filing system, comprising: a storage device for storing a medical image data; a control unit for controlling a matter that the medical image data is displayed on an outside device on the basis of a property of the medical image data; and a display control unit for making the outside device display the medical image data that it is determined to be a display object by the control unit.

To solve the above-described problems, the present invention provides the medical image filing system, comprising: a storage device for storing a medical image data; a control unit for controlling a matter that a reference image data is created on the basis of a property of the medical image data recorded to the storage device, or of the medical image data read out from the storage device; and a reference-image creating unit for creating the reference image data on the bases of the medical image data that it is determined to be a creating object by the control unit.

To solve the above-described problems, the present invention provides the medical image filing method, comprising steps of: (A) primarily storing a medical image data in a primary storage device; (B) controlling a matter that the medical image data is stored in a secondary storage device on the basis of a property of the medical image data recorded to the primary storage device, or of the medical image data read out from the primary storage device; and (c) secondarily storing the medical image data that it is determined to be a storage object by the step (B).

To solve the above-described problems, the present invention provides the medical image filing method, comprising steps of: (A) storing a medical image data in a storage device; (B) controlling a matter that the medical image data is transmitted to an outside device on the basis of a property of the medical image data; and (C) transmitting the medical image data that it is determined to be a transmitting object by the step (B).

To solve the above-described problems, the present invention provides the medical image filing method, comprising steps of: (A) storing a medical image data in a storage device; (B) controlling a matter that the medical image data is displayed on an outside device on the basis of a property of the medical image data; and (C) making the outside device display the medical image data that it is determined to be a display object by the step (B).

To solve the above-described problems, the present invention provides the medical image filing method, comprising steps of: (A) storing a medical image data in a storage device; (B) controlling a matter that a reference image data is created on the basis of a property of the medical image data recorded to the storage device, or of the medical image data read out from the storage device; and (C) creating the reference image data on the bases of the medical image data that it is determined to be a creating object by the step (B).

In addition, the "filing" includes reception of the medical image data read out from a storage device and transmission (transfer) of a medical image data to other storage device. Further, the "filing" includes transmission for displaying a medical image data read out from a storage device on a remote-terminal, a medical image display system.

Therefore, according to the present invention to provide a medical image filing system and a medical image filing method, a medical image data collected by a medical image tomography apparatus of a multi-slice X-ray CT apparatus makes it to filed efficiently. Accordingly, the medical image filing system and the medical image filing method avoid a problem like Shortage of capacity of the storage device, increase costs, delay the reference of image, reduce a network throughput, and refer to unnecessary images.

BRIEF DESCRIPTION OF THE DRAWINGS

In the accompanying drawings:

FIG. 5 is a flow chart showing a transmitting method of the medical image data in the medical image filing method according to the present invention;

FIG. 7 is a sample of a table showing an image management table; and

DESCRIPTION OF THE PREFERRED EMBODIMENTS

A preferred embodiment of a medical image filing system and a medical image filing method according to the present invention will be described with reference to the attached drawings. Note that the medical image filing system according to the present invention is incorporated in a PACS.

Figure 1:
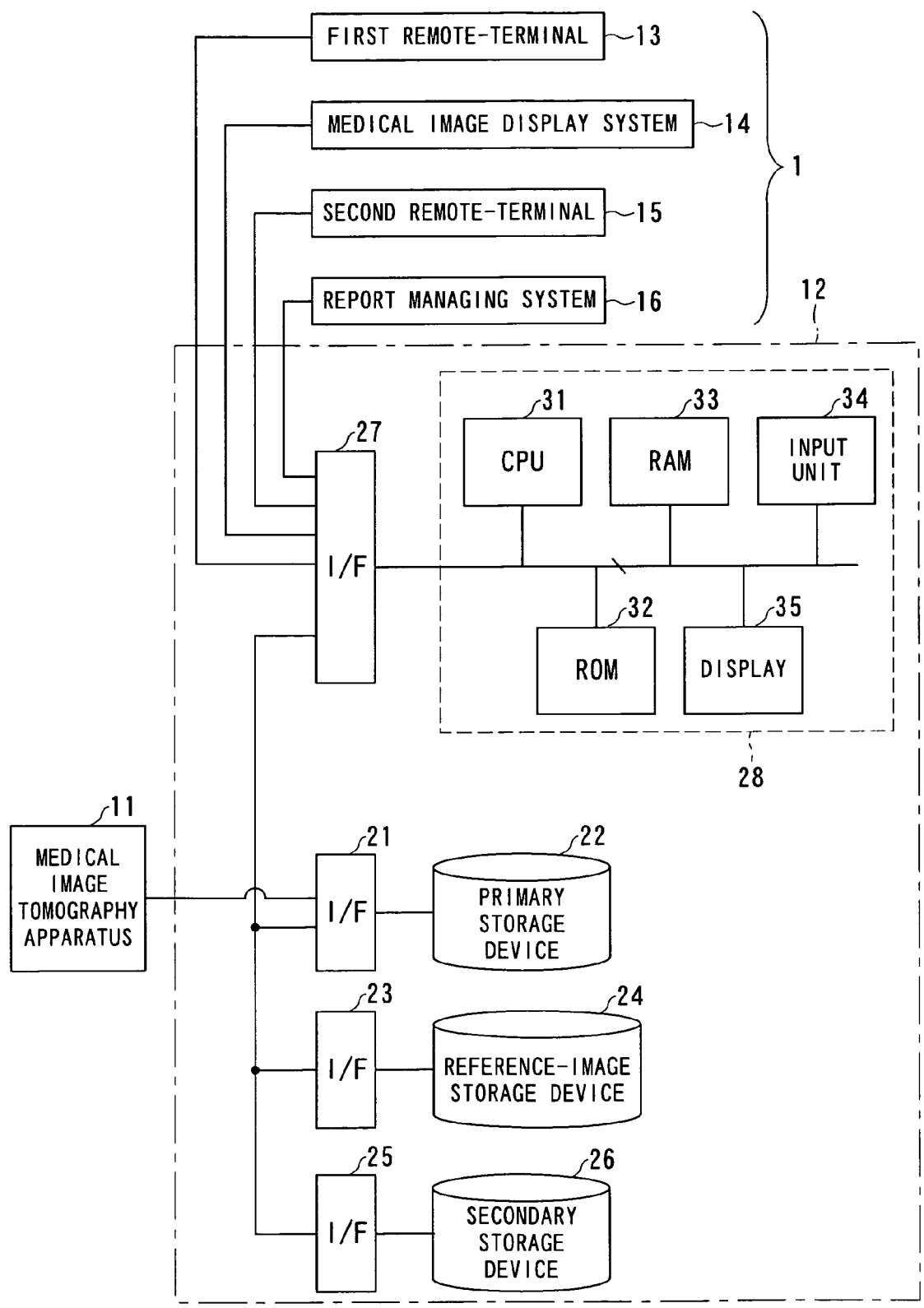
FIG. 1 is a diagram schematically showing a hardware structure of a PACS.

FIG. 1 is a diagram schematically showing the hardware structure of a PACS.

Referring to FIG. 1, the PACS 1 is shown, and is connected to a medical image tomography apparatus (modality) 11 to be communicable therewith. The PACS 1 comprises: a medical image filing system 12; a first remote-terminal 13 (detailed image display system); a medical image display system 14; a second remote-terminal (reference-image display system) 15; and a report managing system 16.

An example of the medical image tomography apparatus 11 is a multi-slice X-ray CT apparatus. With tomography operation of the multi-slice X-ray CT apparatus, a plurality of slice images of a sample are collected. The slice images are transmitted to the medical image filing system 12 in the PACS 1, as image data having a luminance value indicated as the amount of digital data for each pixel.

The medical image filing system 12 comprises: an primary storage device 22 connected thereto via an interface (I/F) 21; a reference-image storage device 24 connected thereto via an interface 23; a secondary storage device 26 connected thereto via an interface 25; and a server 28 connected thereto via an interface 27. Further, the interfaces 21, 23, 25 and 27 are connected to be communicable with each other via the Ethernet (registered trademark), as an example.

In particular, the interface 21 of the primary storage device 22 is connected to the medical image tomography apparatus 11 via a communication line. Via the communication line, digital imaging and communications in medicine (DICOM)-standard-compliant medical image data and incidental information thereto are received from the medical-image tomography apparatus 11.

The primary storage device 22 and the reference-image storage device 24 comprise a fast storing media, such as an HDD. The primary storage device 22 and the reference-image storage device 24 store (save) a recorded medical image data. Note that the primary storage device 22 and the reference-image storage device 24 may comprise one hard disk respectively and, alternatively, a plurality of hard disks. The secondary storage device 26 is called a media, a library device, or an archiving device, and comprises a recording media, such as a tape drive or a digital video (versatile) disk (DVD) autochanger.

The server 28 is a personal computer, and comprises: a central processing unit (CPU) 31; a read only memory (ROM) 32; a Random Access Memory (RAM) 33; an input unit 34; and a display 35.
In addition, obviously, the "filing" includes reception of the medical image data read out from the primary storage device 22 and transmission (transfer) of the medical image data to the reference-image storage device 24 and the secondary storage device 26. Further, the "filing" includes transmission for displaying the medical image data read out from a storage device on the first remote-terminal 13, the medical image display system 14, and the second remote-terminal 15.

The first remote-terminal 13 is a 2D viewer for specifically displaying the image, and is connected to a server 28 to be communicable under an inner protocol of the server 28. In addition, the first remote-terminal 13 makes a report based on the medical image data.

The second remote-terminal 15 is a viewer for displaying the reference image and, similarly, is connected to the server 28 to be communicable under the inner protocol of the server 28.

The medical image display system 14 is a 2D or 3D viewer. The DICOM-standard-compliant medical image data and the incidental information thereto can be transmitted from the medical image filing system 12 to the medical image display system 14.

The report managing system 16 stores the report made by the first remote-terminal 13. In addition, the report managing system 16 transmits information that is specified by the medical image data attached to the report (unique identifier (UID) and so on) to the server 28.

Figure 2:
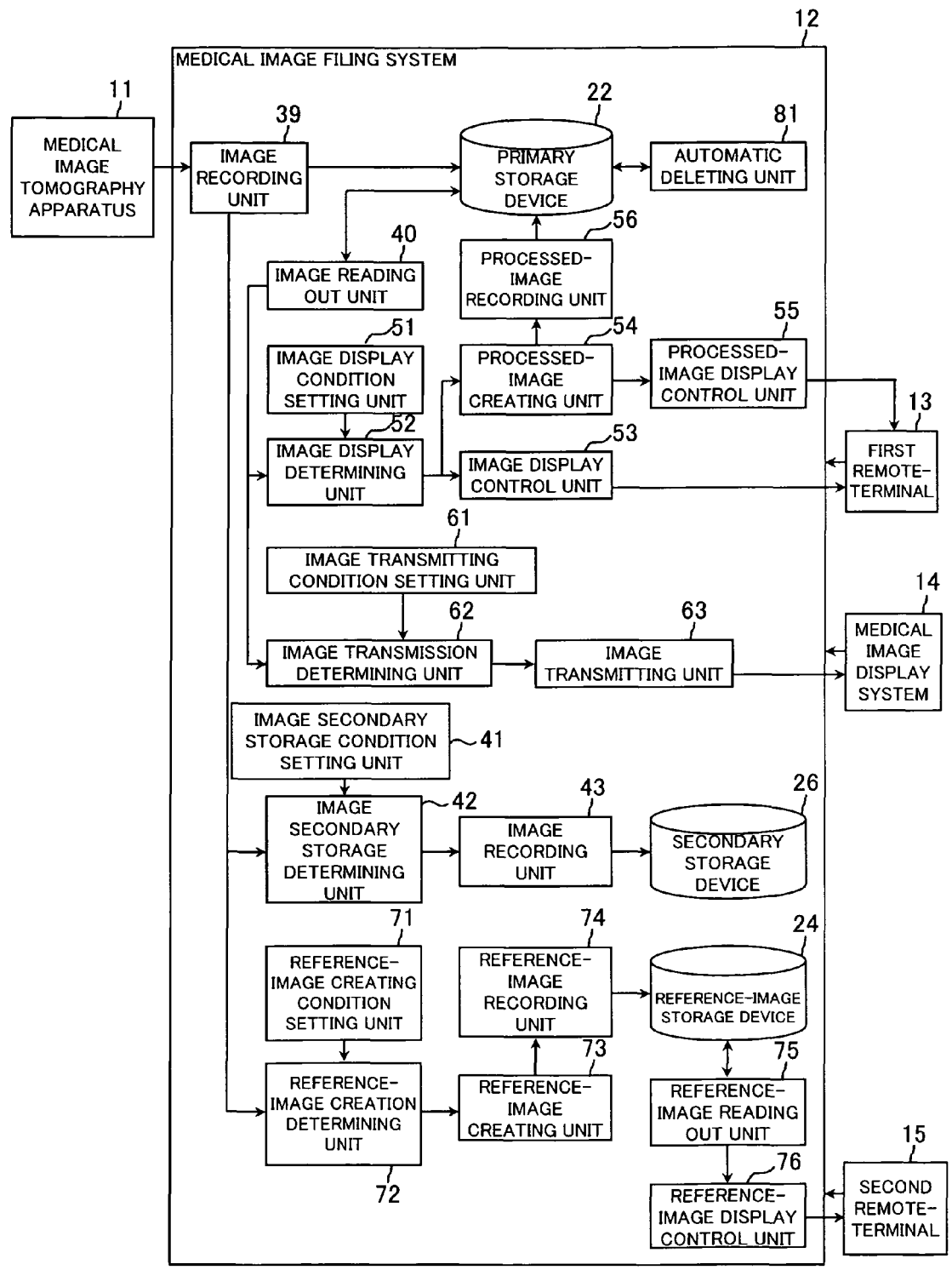
FIG. 2 is a block diagram showing a medical image filing system according to the embodiment of a present invention.

FIG. 2 is a block diagram showing a medical image filing system according to the embodiment of the present invention. Referring to FIG. 2, components function by executing the programs for filing control and image processing pre-stored in the ROM 32 (shown in FIG. 1) by the CPU 31 (shown in FIG. 1). The components shown in FIG. 2 may be provided for the medical image filing system 12, as hardware.
The medical image filing system 12 comprises: an image recording unit 39; and an image reading out unit 40.

The image recording unit 39 has a function for recording all the medical image data received from the medical image tomography apparatus 11 to the primary storage device 22. The primary storage device 22 primarily stores all the medical image data received from the medical image tomography apparatus 11 by recording at the image recording unit 39.

The image reading out unit 40 has a function for reading out the medical image data stored in the primary storage device 22.

The medical image filing system 12 comprises: an image secondary storage condition setting unit 41; an image secondary storage determining unit 42; and an image recording unit 43.

The image secondary storage condition setting unit 41 has a function for presetting a secondary storage condition to secondarily store the medical image data to the secondary storage device 26. The secondary storage condition is set on the basis of the property (type) of the medical image data, e.g., a medical image except for a CT image, a CT slice image with a slice thickness of 5 mm or more, and a CT image except for a slice image. Further, the secondary storage condition may be set on the basis of information of a reconstruction function, MPR and a comment, as a property of the medical image data. Furthermore, the secondary storage condition is pre-stored in the ROM 32 and so on.

The image secondary storage determining unit 42 has a function for determining whether or not the medical image data recorded to the primary storage device 22 by the image recording unit 39 satisfies the secondary storage condition set by the image secondary storage condition setting unit 41. In other words, the image secondary storage determining unit 42 determines whether or not the medical image data recorded to the primary storage device 22 is the medical image data of a secondary storage object.

The image recording unit 43 has a function for recording the medical image data of the secondary storage object to the secondary storage device 26. The secondary storage device 26 secondarily stores only medical image data of the secondary storage object by recording at the image recording unit 43.

In addition, the image secondary storage determining unit 42 may determine whether or not the medical image data read out from the primary storage device 22 by the image reading out unit 40 is the medical image data of the secondary storage object.

The medical image filing system 12 comprises: an image display condition setting unit 51; an image display determining unit 52; an image display control unit 53; a processed-image creating unit 54; a processed-image display control unit 55; and a processed-image recording unit 56.

The image display condition setting unit 51 has a function for presetting a display condition to display the medical image data on the first remote-terminal 13. The display condition is set on the basis of a property of the medical image data, e.g., a medical image except for a CT image, a CT slice image with a slice thickness of 5 mm or more, and a CT image except for a slice image. Further, the display condition data may be set on the basis of information of a reconstruction function, MPR and a comment, as a property of the medical image data. Furthermore, the display condition is pre-stored in the ROM 32 and so on.

The image display determining unit 52 has a function for determining whether or not the medical image data read out from the primary storage device 22 by the image reading out unit 40 satisfies the display condition set by the image display condition setting unit 51. In other words, the image display determining unit 52 determines whether or not the medical image data read out from the primary storage device 22 is the medical image data of a display object.

The image display control unit 53 has a function for making the first remote-terminal 13 display the medical image data of the display object. The first remote-terminal 13 displays only medical image data of the display object. The medical image data of the display object is displayed on the first remote-terminal 13, as an image which Web technology and so on is used for.

The processed-image creating unit 54 has a function for creating processed image data as the medical image data with image processing, such as MPR image processing, to a raw data contained in the medical image data of a non-display object.

The processed-image display control unit 55 has a function for making the first remote-terminal 13 display the processed image data created by the processed image creating unit 54. The first remote-terminal 13 displays the processed image data as the medical image data. The processed image data is displayed on the first remote-terminal 13, as an image which Web technology and so on is used for.

The processed-image recording unit 56 has a function for recording, to the primary storage device 22, the processed-image data created by the processed-image creating unit 54. The primary storage device 22 stores the processed image data as the medical image data by recording at the processed-image recording unit 56.

The medical image filing system 12 comprises: an image transmitting condition setting unit 61; an image transmission determining unit 62; and an image transmitting unit 63.

The image transmitting condition setting unit 61 has a function for presetting an image transmitting condition to transmit (transfer) the medical image data to the medical image display system 14. The image transmitting condition is set on the basis of property of the medical image data, e.g., a medical image except for a CT image, a CT slice image with a slice thickness of 5 mm or more, and a CT image except for a slice image. Further, the image transmitting condition may be set on the basis of information of a reconstruction function, MPR and a comment, as a property of the medical image data. Furthermore, the transmitting condition is pre-stored in the ROM 32 and so on.

The image transmitting determining unit 62 has a function for determining whether or not the medical image data read out from the primary storage device 22 by the image reading out unit 40 satisfies the transmitting condition set by the image transmitting condition setting unit 61. In other words, the image transmitting determining unit 62 determines whether or not the medical image data read out from the primary storage device 22 is the medical image data of a transmitting object.

The image transmitting unit 63 has a function for sending the medical image data of the transmitting object to the medical image display system 14. Only medical image data of the transmitting object is transmitted to the medical image display system 14.

In addition, the medical image filing system 12 comprises: a reference-image creating condition setting unit 71; a reference-image creation determining unit 72; a reference-image creating unit 73; a reference-image recording unit 74; a reference-image reading out unit 75; and a reference-image display control unit 76.

The reference-image creating condition setting unit 71 has a function for presetting a creating condition to create the reference image data (electronic medical chart and so on) on the basis of the medical image data. The creating condition is set on the basis of a property of the medical image data, e.g., a medical image except for a CT image, a CT slice image with a slice thickness of 5 mm or more, and a CT image except for a slice image. Further, the creating condition may be set on the basis of information of a reconstruction function, MPR and a comment, as a property of the medical image data. Furthermore, the creating condition is pre-stored in the ROM 32 and so on.

The reference-image creation determining unit 72 has a function for determining whether or not the medical image data recorded in the primary storage device 22 by the image recording unit 39 satisfies the creating condition set by the reference-image creating condition setting unit 71. In other words, the reference-image creation determining unit 72 determines whether or not the medical image data recorded to the primary storage device 22 is the medical image data of a creating object.

The reference-image creating unit 73 has a function for creating the reference image data on the basis of the medical image data of a creating object. The reference image data is created on the basis of only medical image data of the creating object by creating the reference image data at the reference-image creating unit 73.

The reference-image recording unit 74 has a function for storing the reference image data created by the reference-image creating unit 73 to the reference-image storage device 24. The reference-image storage device 24 stores the reference image data on the basis of only medical image data of the creating object by recording at the reference-image recording unit 74.

The reference-image reading out unit 75 has a function for reading out the reference image data stored in the reference-image storage device 24.

The reference-image display control unit 76 has a function for making the second remote-terminal 15 display the reference image data read out by the reference-image reading out unit 75. The second remote-terminal 15 displays the reference image data on the basis of only medical image data of the creating object. The reference image data is displayed on the second remote-terminal 15, as an image which Web technology and so on is used for.

In addition, the reference-image creation determining unit 72 may determine whether or not the medical image data read out from the primary storage device 22 by the image reading out unit 40 is the medical image data of the creating object.

The medical image filing system 12 comprises an automatic deleting unit 81 that deletes all the medical image data stored in the primary storage device 22 from the primary storage device 22, after a predetermined time period from recording by the image recording unit 39. The automatic deleting unit 81 may delete only the medical image data of a deleting object in all the medical image data stored in the primary storage device 22 from the primary storage device 22, after a predetermined time period from recording by the image recording unit 39.

The automatic deleting unit 81 may delete the medical image data which don't satisfy the secondary storage condition in all the medical image data from the primary storage device 22, after a predetermined time period from recording by the image recording unit 39.

The automatic deleting unit 81 may delete the medical image data which don't satisfy the display condition in all the medical image data from the primary storage device 22, after a predetermined time period from recording by the image recording unit 39.

The automatic deleting unit 81 may delete the medical image data which don't satisfy the transmitting condition in all the medical image data from the primary storage device 22, after a predetermined time period from recording by the image recording unit 39.

The automatic deleting unit 81 may delete the medical image data which don't satisfy the creating condition in all the medical image data from the primary storage device 22, after a predetermined time period from recording by the image recording unit 39.

The first remote-terminal 13 makes the report on the basis of the medical image data displayed on the medical image filing system 12. The report made by the first remote-terminal 13 is stored in the report managing system 16 (shown in FIG. 1). At the same time, the information which is specified by the medical image data attached on the report (UID and so on) is transmitted to the medical image filing system 12, is given on an image management table (shown in FIG. 7). The image secondary storage determining unit 42 may determine whether or not the medical image data is the secondary storage object on the basis of the information given on the image management table. The reference-image creation determining unit 72 may determine whether or not the medical image data is the creating object on the basis of the information given on the image management table. The automatic deleting unit 81 may determine whether or not the medical image data is the deleting object on the basis of the information attached on the report.

Next, it explains about a preferred embodiment of a medical image filing method according to the present invention, with referring to flow charts that showed it in the FIG. 3-6.

Figure 3:
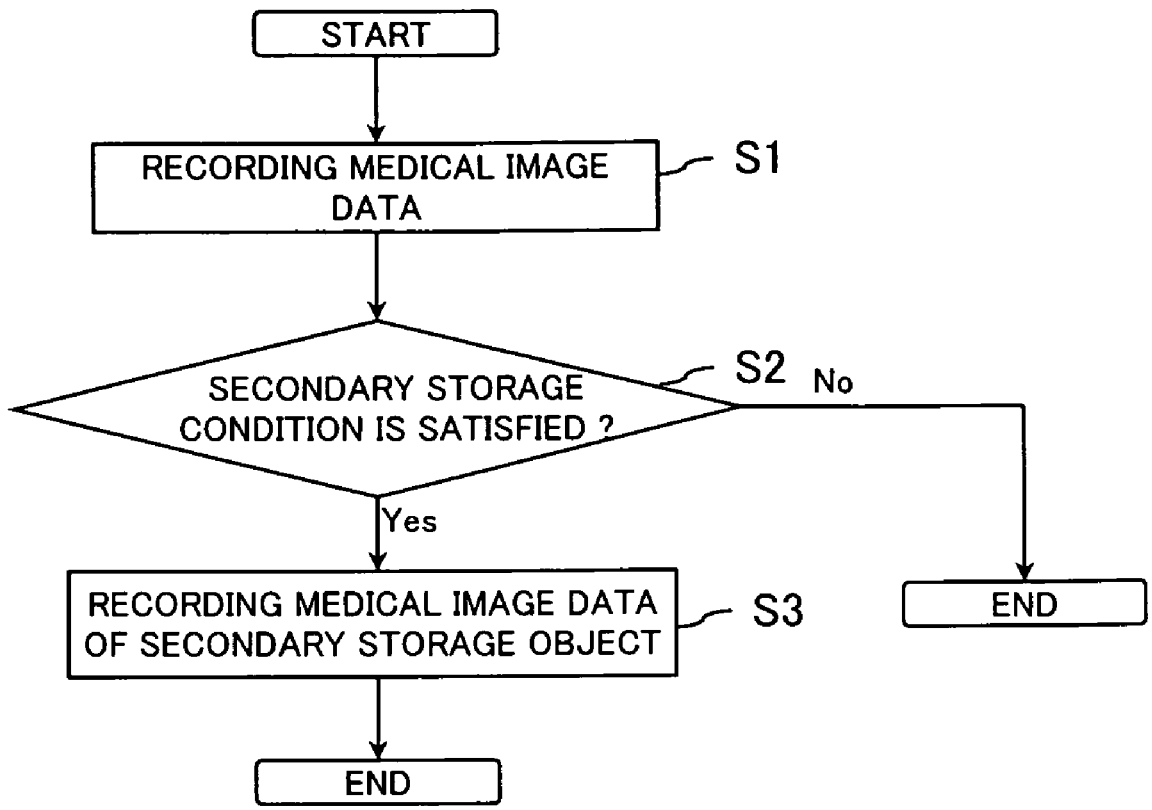
FIG. 3 is a flow chart showing a secondary storage method of the medical image data in the medical image filing method according to the present invention.

FIG. 3 is a flow chart showing a secondary storage method of the medical image data in the medical image filing method according to the present invention.

All the medical image data received from the medical image tomography apparatus (multi-slice X-ray CT apparatus) 11 is recorded to the primary storage device 22 (step S1). Accordingly, all the medical image data received from the medical image tomography apparatus 11 is primarily stored (saved) in the primary storage device 22.

Subsequently, it is determined whether or not each medical image data recorded to the primary storage device 22 by the step S1 satisfies the secondary storage condition (step S2). In other words, it is determined whether or not each medical image data recorded to the primary storage device 22 by the step S1 is the medical image data of the secondary storage object. In the step S2, it is determined on the basis of the incidental information, as the DICOM-standard, added to each medical image data, whether or not the medical image data recorded to the primary storage device 22 by the step S1 satisfies the secondary storage condition. It may be determined whether or not each medical image data stored in the primary storage device 22 is the medical image data of the secondary storage object.

The medical image data determined "Yes" by the step S2 is determined the medical image data of the secondary storage object. The medical image data of the secondary storage object is recorded to the secondary storage device 26 (step S3).

On the other hand, the medical image data determined "No" by the step S2 is determined the medical image data of the non-secondary storage object. The medical image data of the non-secondary storage object does not be recorded to the secondary storage device 26. Accordingly, only medical image data of the secondary storage object is secondarily stored in the secondary storage device 26.

Note that the function of the secondary storage determining unit 42 may be OFF and all the medical image data may automatically be recorded to the secondary storage device 26. The ON/OFF operation of the image secondary storage determining unit 42 may be determined depending on the hospital case.

Further, even if the medical image data does not satisfy the secondary storage condition, the image secondary storage determining unit 42 may record the medical image data to the secondary storage device 26 in accordance with an instruction. For example, the medical image data in this case corresponds to a rare case that needs the creation of the processed image data after a while.

Figure 4:
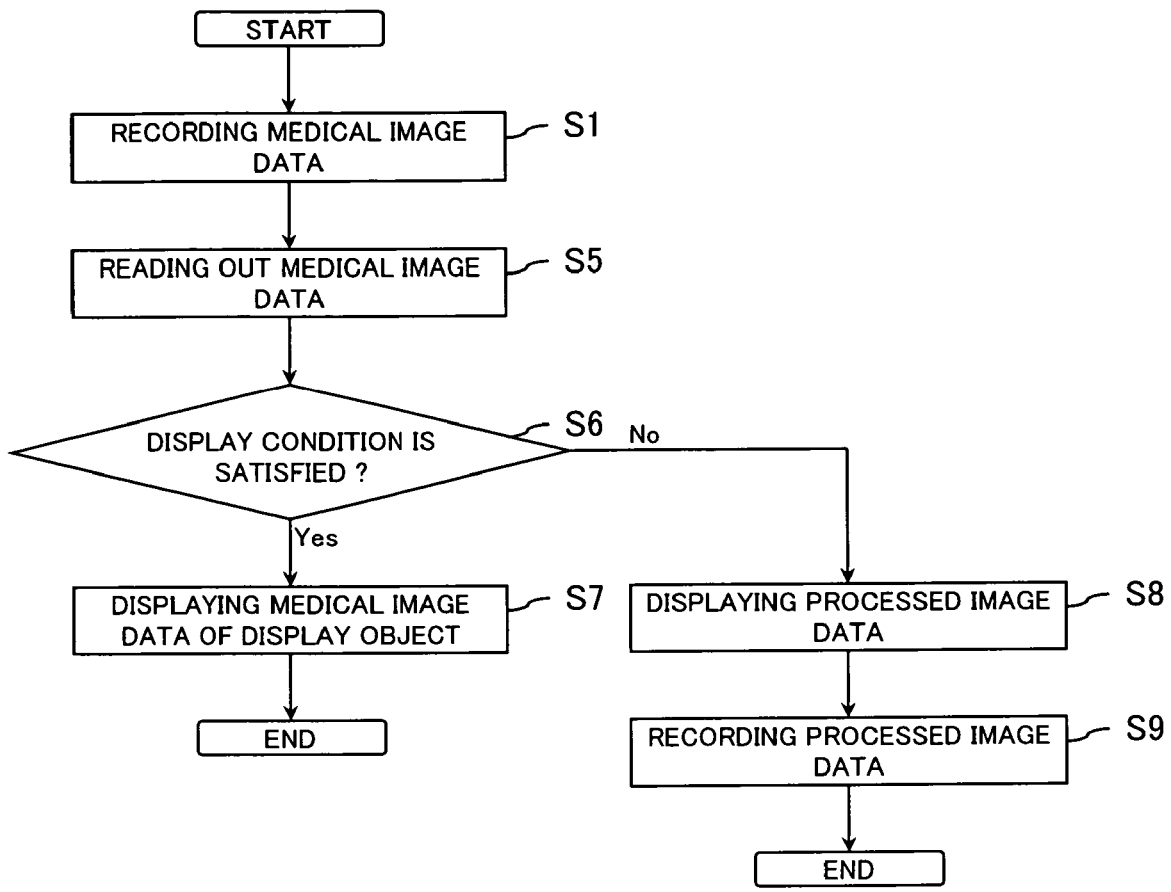
FIG. 4 is a flow chart showing a display method of the medical image data in the medical image filing method according to the present invention.

FIG. 4 is a flow chart showing a display method of the medical image data in the medical image filing method according to the present invention.

All the medical image data received from the medical image tomography apparatus 11 is recorded to the primary storage device 22 (step S1). Accordingly, all the medical image data received from the medical image tomography apparatus 11 is primarily stored in the primary storage device 22.

Subsequently, when the medical image filing system 12 receives a request for the detailed image display from the first remote-terminal 13, all the medical image data that cope with the request for the detailed image display is read out from the primary storage device 22 (step S5).

It is determined whether or not each medical image data read out from the primary storage device 22 by the step S5 satisfies the display condition (step S6). In other words, it is determined whether or not each medical image data read out from the primary storage device 22 by the step S5 is the medical image data of the display object. In the step S6, it is determined on the basis of incidental information, as the DICOM-standard, added to each medical image data, whether or not the medical image data read out from the primary storage device 22 by the step S5 satisfies the display condition.

The medical image data determined "Yes" by the step S6 is determined the medical image data of the display object. The medical image data of the display object is displayed on the first remote-terminal 13 (step S7). In other words, only the medical image data of the display object in the medical image data required by the first remote-terminal 13 is displayed on the first remote-terminal 13. The medical image data of the display object is displayed on the first remote-terminal 13, as an image that Web technology and so on is used for.

On the other hand, the medical image data determined "No" by the step S6 is determined the medical image data of the non-display object. The processed image data as the medical image data is created with image processing, such as MPR image processing, to the raw data contained in the medical image data of the non-display object. The processed image data as the medical image data is displayed on the first remote-terminal 13 display (step S8).

Further, the processed image data as the medical image data can be recorded to the primary storage device 22 in accordance with an instruction (step S9). The processed image data recorded by the step S9 is used as well as the medical image data recorded by the step S1, that is, it determine whether or not the processed image data satisfies the secondary storage condition, the display condition, the transmitting condition, and the creating condition. Subsequently, the processed image data is the secondarily stored, is transmitted, and the reference image is created.

FIG. 5 is a flow chart showing a transmitting method of the medical image data in the medical image filing method according to the present invention.

All the medical image data received from the medical image tomography apparatus 11 is recorded to the primary storage device 22 (step S1). Accordingly, all the medical image data received from the medical image tomography apparatus 11 is primarily stored in the primary storage device 22.

Subsequently, when the medical image filing system 12 receives a request for transmitting image from the medical image display system 14, all the medical image data that cope with the request for the transmitting image display is read out from the primary storage device 22 (step S10).

It is determined whether or not each medical image data read out from the primary storage device 22 by the step S10 satisfies the transmitting condition (step S11). In other words, it is determined whether or not each medical image data read out from the primary storage device 22 by the step S10 is the medical image data of the transmitting object. In the step S11, it is determined on the basis of the incidental information, as the DICOM-standard, added to each medical image data, whether or not the medical image data read out from the primary storage device 22 by the step S10 satisfies the transmitting condition.

The medical image data determined "Yes" by the step S11 is determined the medical image data of the transmitting object. The medical image data of the transmitting object is transmitted to the medical image display system 14 (step S12).

On the other hand, the medical image data determined "No" by the step S11 is determined the medical image data of the non-transmitting object. The medical image data of the non-transmitting object is not transmitted to the medical image display system 14. In other words, only the medical image data of the transmitting object in the medical image data required by the medical image display system 14 is transmitted to the medical image display system 14.

Figure 6:
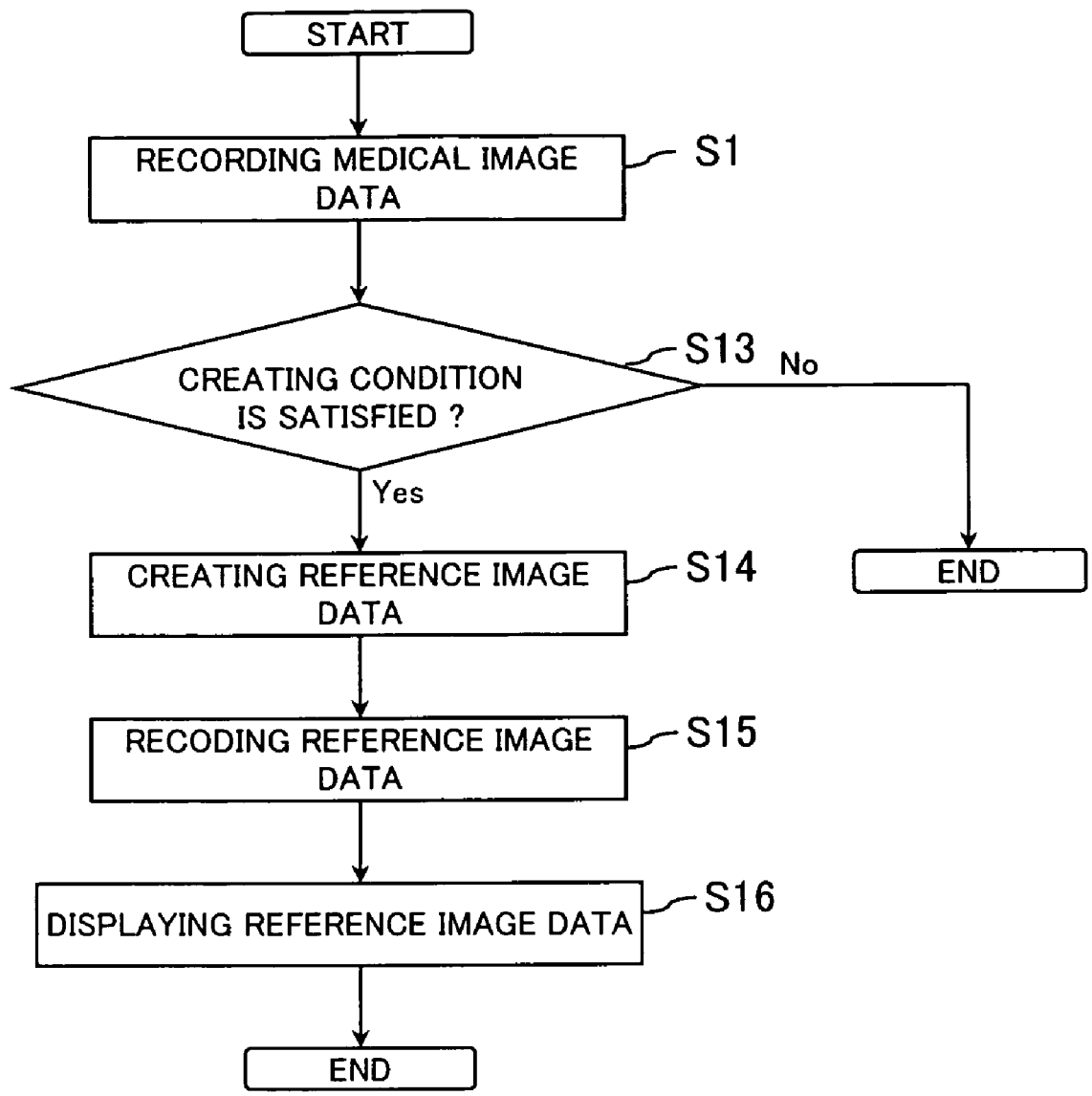
FIG. 6 is a flow chart showing a creating reference-image method of the medical image data in the medical image filing method according to the present invention.
Figure 8:
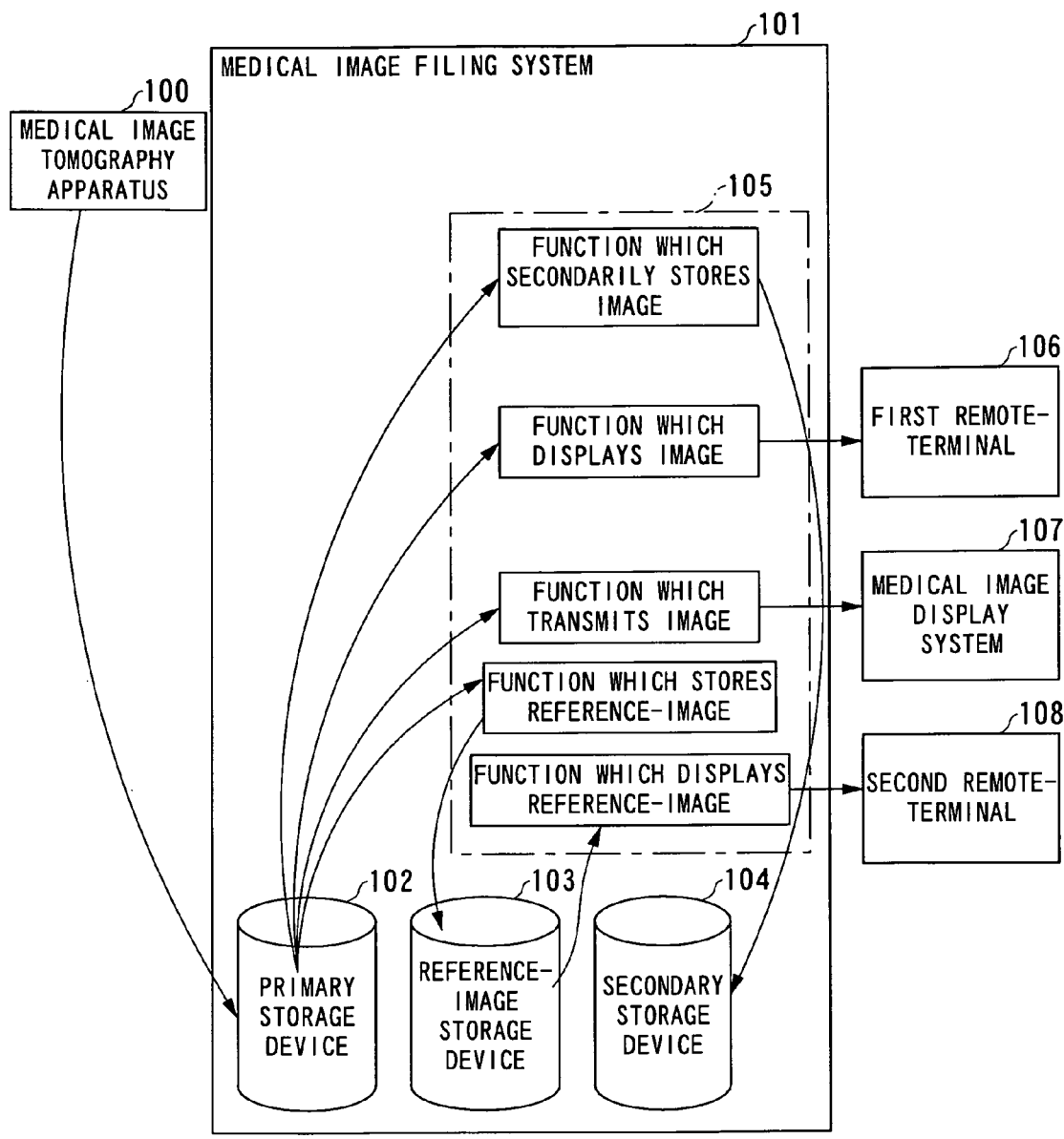
FIG. 8 is a block diagram showing the entire structure of a PACS using a conventional medical image filing system.

FIG. 6 is a flow chart showing a creating reference-image method of the medical image data in the medical image filing method according to the present invention.

All the medical image data received from the medical image tomography apparatus 11 is recorded to the primary storage device 22 (step S1). Accordingly, all the medical image data received from the medical image tomography apparatus 11 is primarily stored (saved) in the primary storage device 22.

Subsequently, it is determined whether or not each medical image data recorded to the primary storage device 22 by the step S1 satisfies the creating condition (step S13). In other words, it is determined whether or not each medical image data recorded to the primary storage device 22 by the step S1 is the medical image data of the creating object. In the step S13, it is determined on the basis of the incidental information, as the DICOM-standard, added to each medical image data, whether or not the medical image data recorded to the primary storage device 22 by the step S1 satisfies the creating condition. It may be determined whether or not each medical image data stored in the primary storage device 22 is the medical image data of the creating object.

The medical image data determined "Yes" by the step S13 is determined the medical image data of the creating object. The reference image data is created on the basis of the medical image data of the creating object (step S14). The reference image data is recorded to the reference-image storage device 24 (step S15).

On the other hand, the medical image data determined "No" by the step S13 is determined the medical image data of the non-creating object. The reference image data is not created on the basis of the medical image data of the non-creating object.

Further, when the medical image filing system 12 receives a request for the reference image display from the second remote-terminal 15, all the medical image data that cope with the request for the reference image display is read out from the reference-image storage device 24. The medical image data read out from the reference-image storage device 24 is displayed on the second remote-terminal 15 (step S16). The medical image data of the creating object is displayed on the second remote-terminal 15, as an image that Web technology and so on is used for.

The medical image data stored in the primary storage device 22 may be deleted from the primary storage device 22, after a predetermined time period from recording.

The report is made on the basis of the medical image data by the first remote-terminal 13. The report made by the first remote-terminal 13 is stored in the report managing system 16 (shown in FIG. 1). At the same time, the information which is specified by the medical image data attached on the report (UID and so on) is transmitted to the medical image filing system 12, is given on the image management table.

FIG. 7 is a sample of a table showing the image management table.

Each medical image data on the image management table is given the information. For example, UID "1.2.8329.1" is the medical image data created by "CT" apparatus and be a slice thickness of "5" mm. And UID "1.2.8329.1" is the medical image data of the secondary storage object, of the creating object, of a non-processing object, and of the deleting object.

It may determine whether or not the medical image data is the secondary storage object on the basis of the information given on the image management table, in the step S2. It may determine whether or not the medical image data is the creating object on the basis of the information given on the image management table, in the step S13. It may determine whether or not the medical image data is the deleting object on the basis of the information given on the image management table.

In the medical image filing system 12 and the medical image filing method according to the present invention, the image secondary storage determining unit 42 can store only the medical image data that needs the permanent storage (permanent archive) to the secondary storage device 26. Therefore, the media used as the secondary storage device 26 can be saved.

In addition, in the medical image filing system 12 and the medical image filing method according to the present invention, the automatic deleting unit 81 deletes the medical image data that does not need the permanent storage from the primary storage device 22 after a predetermined time period. Therefore, the memory capacity of the primary storage device 22 can be saved while the image processing after the tomography of the image is possible.

In addition, in the medical image filing system 12 and the medical image filing method according to the present invention, the image transmission determining unit 62 can transmit only the thick-slice image to the medical image display system 14 that needs only the thick-slice image and can transmit all the medical image data to the medical image display system 14 (e.g., 3D image creating apparatus) that needs both the thick-slice image and the thin-slice image. Therefore, the increase in network load due to the transfer of unnecessary data can be suppressed or can be reduced.

In addition, in the medical image filing system 12 and the medical image filing method according to the present invention, the image display determining unit 52 can transfer and display only the data processed by the MPR processing of a large number of thin-slice images. Thus, the network load can be reduced and an operator can refer to a necessary image fast with the best method.

In addition, in the medical image filing system 12 and the medical image filing method according to the present invention, the processed-image storing unit 56 can easily display the past processed-image and the current processed-image in the comparison with the past image and the interpretation, and further can refer to the created processed-image by the in-hospital distribution.

In addition, in the medical image filing system 12 and the medical image filing method according to the present invention, the reference-image creation determining unit 72 can reduce the load of the medical image filing system 12 and the network load and can distribute only the image necessary for a user, as a reference image, because unnecessary reference-image data is not created.

The medical image filing system 12 according to the present invention is not limited to the above-mentioned structure example, and can be properly changed without departing the essentials of claims.

What is claimed is:

1. A medical image filing system comprising:
a primary storage device primarily storing medical image data;
an image recording unit recording all the medical image data received from a medical image apparatus to the primary storage device;
a secondary storage device secondarily storing the medical image data;
an image secondary condition setting unit presetting a condition to secondarily store the medical image data to the secondary storage device based on a thickness of a slice thickness of the medical image data having a slice thickness larger than a predetermined value; and
an image secondary storage determining unit configured to determine whether the medical image data stored in the primary storage device by the image recording unit satisfies the condition of a thickness of a slice thickness of the medical image data being larger than the predetermined value for storage in the secondary storage device,
wherein the medical image data with the thinner-slice-thickness and a processed image data created on the basis of the medical image data with the thinner-slice-thickness are stored in the primary storage device, the image secondary storage determining unit further controls storage of the processed image data in the secondary storage device and non-storage of the medical image data with the thinner-slice-thickness.

2. The medical image filing system according to claim 1, wherein the image secondary storage determining unit further controls storage of the medical image data with a thicker-slice-thickness which has a slice thickness of the predetermined value or more in the secondary storage device, and non-storage of the medical image data with a thinner-slice-thickness which has the slice thickness thinner than the predetermined value.

3. The medical image filing system according to claim 2, wherein the image secondary storage determining unit further controls deletion of the medical image data with the thinner-slice-thickness from the primary storage device, after a predetermined time period from recording.

4. The medical image filing system according to claim 1, wherein the image secondary storage determining unit further controls deletion of the medical image data with the thinner-slice-thickness from the primary storage device, after a predetermined time period from recording.

5. The medical image filing system according to claim 1, wherein the image secondary storage determining unit further controls deletion of the medical image data that is determined to be a non-storage object from the primary storage device, after a predetermined time period from recording.

6. The medical image filing system according to claim 1, further comprising:
a display configured to display incidental information of the medical image data stored in the primary storage device; and
an input unit configured to instruct the medical image data stored in the primary storage device,
wherein the image secondary storage determining unit further controls storage of the medical image data specified by an input unit in the secondary storage device regardless of the property.

7. The medical image filing system according to claim 1, wherein the image secondary storage determining unit further controls storage of the medical image data on the bases of at least one of a reconstruction function, a data of MPR, or a comment.

8. A medical image filing system comprising:
a storage device storing a medical image data;
an image transmitting condition setting unit presetting a condition to transmit the medical image data to an outside device based on a thickness of slice thickness of the medical image data having a slice thickness larger than a predetermined value;
an image transmission determining unit configured to determine whether the medical image data is transmitted to the outside device on the basis of satisfying the condition of a thickness of a slice thickness of the medical image data being larger than the predetermined value; and
a transmitting unit for transmitting the medical image data that is determined to be transmitted by the image transmission determining unit to the outside device,
wherein the medical image data with the thinner-slice-thickness and a processed image data created on the basis of the medical image data with the thinner-slice-thickness are stored in the storage device, the image transmission determining unit further controls transmission of the processed image data and non-transmission of the medical image data with the thinner-slice-thickness.

9. The medical image filing system according to claim 8, wherein the image transmission determining unit further controls transmission of the medical image data with a thicker-slice-thickness which has a slice thickness of the predetermined value or more, and non-transmission of the medical image data with a thinner-slice-thickness which has the slice thickness thinner than the predetermined value.

10. The medical image filing system according to claim 9, wherein the image transmission determining unit further controls deletion of the medical image data with the thinner-slice-thickness from the storage device, after a predetermined time period from recording.

11. The medical image filing system according to claim 8, wherein the image transmission determining unit further controls deletion of the medical image data with the thinner-slice-thickness from the storage device, after a predetermined time period from recording.

12. The medical image filing system according to claim 8, wherein the image transmission determining unit further controls deletion of the medical image data that is determined to be a non-transmitting object from the storage device, after a predetermined time period from recording.

13. The medical image filing system according to claim 8, further comprising:
a display configured to display incidental information of the medical image data stored in the storage device; and
an input unit configured to instruct the medical image data stored in the storage device,
wherein the image transmission determining unit further controls transmission of the medical image data specified by the input unit regardless of the property.

14. The medical image filing system according to claim 8, wherein the image transmission determining unit further controls transmission of the medical image data on the bases of at least one of a reconstruction function, a data of MPR, or a comment.

15. A medical image filing system comprising:
   a storage device storing a medical image data;
   a reference image creating condition setting unit presetting a condition to create the medical image data based on a thickness of slice thickness of the medical image data having a slice thickness larger than a predetermined value;
   a reference image creation determining unit configured to determine whether the medical image data is displayed on an outside device on the basis of satisfying the condition of a thickness of a slice thickness of the medical image data being larger than a predetermined value; and
   a reference image display control unit configured to control the outside device display of the medical image data that is determined to be displayed by the reference image creation determining unit,
   wherein the reference image creation determining unit displays the medical image data with a thicker-slice-thickness which has a slice thickness of a predetermined value or more, and does not display the medical image data with a thinner-slice-thickness which has the slice thickness thinner than the predetermined value, and wherein the medical image data with a thinner-slice-thickness and a processed image data created on the basis of the medical image data with the thinner-slice-thickness are stored in the storage device, the reference image creation determining unit further controls display of the processed image data and non-display of the medical image data with the thinner-slice-thickness.

16. The medical image filing system according to claim 15, wherein the reference image creation determining unit further controls deletion of the medical image data with a thinner-slice-thickness from the storage device, after a predetermined time period from recording.

17. The medical image filing system according to claim 15, wherein the reference image creation determining unit further controls deletion of the medical image data with the thinner-slice-thickness from the storage device, after a predetermined time period from recording.

* * * * *